| United States Patent [19] | [11] | 4,055,536 |
|---|---|---|
| Soma et al. | [45] | Oct. 25, 1977 |

[54] 4,4'-BIPIPERIDYLIDENE DERIVATIVES AND THEIR USE AS STABILIZERS

[75] Inventors: Nobuo Soma; Takao Yoshioka; Tomoyuki Kurumada; Syoji Morimura, all of Tokyo, Japan

[73] Assignee: Sankyo Company Limited, Tokyo, Japan

[21] Appl. No.: 710,313

[22] Filed: July 30, 1976

[30] Foreign Application Priority Data

Aug. 8, 1975 United Kingdom ............... 33228/75

[51] Int. Cl.² .................... C07D 401/04; C08J 3/20
[52] U.S. Cl. .................... 260/45.8 N; 260/293.63; 260/293.64

[58] Field of Search ............ 260/45.8 N, 293.63, 260/293.64

*Primary Examiner*—Henry R. Jiles
*Assistant Examiner*—Robert T. Bond
*Attorney, Agent, or Firm*—Toren, McGeady and Stanger

[57] ABSTRACT

New 2,2',6,6'-tetraalkyl-2,2',6,6'-tetramethyl-4,4'-bipiperidylidene derivatives, which are optionally substituted in the 1,1',3,3',5, and 5' positions are useful as stabilizers of organic substrates, particularly synthetic polymers, against photo- and thermal-deterioration. They may be prepared by condensing a corresponding 2,6-dialkyl-2,6-dimethyl-4-piperidone and then optionally introducing the desired substituents at the 1- and 1'-positions in the resulting bipiperidylidene derivative.

13 Claims, No Drawings

4,4'-BIPIPERIDYLIDENE DERIVATIVES AND THEIR USE AS STABILIZERS

BACKGROUND OF THE INVENTION

1. Field of the Invention

The present invention relates to certain novel 4,4'-bipiperidylidine derivatives and to their use as stabilizers for various organic sbstrates.

2. Description of the Prior Art

Many organic substrates, particularly polymers, both natural and synthetic, are subject to deterioration in their appearance and/or physical properties when exposed to light and/or heat. customary to incorporate into such substrates various compounds designed to prevent this deterioration; such compounds are known as "polymer stabilizers". A number of piperidine derivatives are known in the prior art to be useful as polymer stabilizers.

BRIEF SUMMARY OF INVENTION

It is an object of the present invention to provide certain novel 4,4'-bipiperidylidine derivatives.

It is a further object of the invention to provide a composition stabilized against photo- and thermal-deterioration comprising an organic substrate and, as stabilizer, a 4,4'-bipiperidylidene derivative.

The novel 4,4'-bipiperidylidene derivatives of the invention have the formula (I):

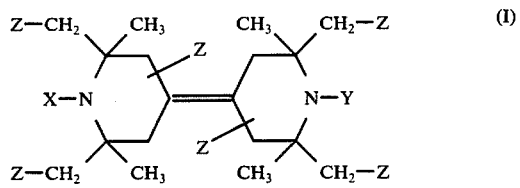

wherein:
each of the symbols Z represents a hydrogen atom or an alkyl group; and X and Y may be the same or different and each represents a hydrogen atom, an oxyl group, a hydroxy group, an alkyl group, an alkenyl group, an alkoxyalkyl group, a cyanoalkyl group, an aliphatic acyl group, a 2,3-eoxypropyl group, an aralkyl group which may optionally be substituted in its aryl moiety, a group of the formula —$CH_2CH(R^1)OR^2$ (wherein $R^1$ represents a hydrogen atom, a methyl group or a phenyl group; and $R^2$ represents a hydrogen atom, or an aliphatic, aromatic, araliphatic or alicyclic acyl group), a group of the formula —$CH_2COOR^3$ (wherein $R^3$ represents an alkyl group, an alkenyl group, a phenyl group, an aralkyl group or a cyclohexyl group), or a group of the formula -$COOR^4$ (wherein $R^4$ represents an alkyl group, a benzyl group, a phenyl group or a cyclohexyl group);
and acid addition salts thereof.

In the case of the two symbols Z linked directly to the piperidine nuclei, each may be attached to either of the carbon atoms adjacent the double-bonded carbon atom in its respective nucleus.

DETAILED DESCRIPTION OF INVENTION

In formula (I), when Z is an alkyl group it may suitably be a lower alkyl group having from 1 to 3 carbon atoms, i.e., methyl, ethyl, propyl or isopropyl, and is preferably methyl.

When X or Y is an alkyl group, it may suitably be one having from 1 to 18 carbon atoms, e.g., methyl, ethyl, propyl, butyl, hexyl, octyl, decyl, hexadecyl or octadecyl; and it is preferably a lower alkyl group having from 1 to 4 carbon atoms, most preferably methyl.

When X or Y is an alkenyl group, it may suitably be one having from 3 to 6 carbon atoms, e.g., allyl, 2-butenyl or 2-hexenyl; and it is preferably one having 3 or 4 carbon atoms, most preferably allyl.

When X or Y is an alkoxyalkyl group, it may suitably be one having from 1 to 3 carbon atoms in its alkyl moiety and from 1 to 18 carbon atoms in its alkoxy moiety, e.g., methoxymethyl, ethoxymethyl, 2-methoxyethyl, 2-ethoxyethyl, 2-butoxyethyl, 2-octoxyethyl, 2-decyloxyethyl, 2-hexadecyloxyethyl, 2-octadecyloxyethyl, 3-butoxypropyl or 2-ethoxypropyl; and it is preferably an alkoxyethyl group having from 1 to 18 carbon atoms in its alkoxy moiety.

When X or Y is a cyanoalkyl group, it may suitably be one having 2 or 3 carbon atoms, e.g. cyanomethyl or 2-cyanoethyl.

When X or Y is an aliphatic acyl group, it may suitably be a saturated or unsaturated one having up to 12 carbon atoms, e.g., an alkanoyl or alkenoyl group, such as, formyl, acetyl, propionyl, butyryl, capryloyl, lauroyl, acryloyl or crotonoyl; and it is preferably an alkanoyl group having from 2 to 4 carbon atoms or an alkenoyl group having 3 or 4 carbon atoms, most preferably acetyl, acryloyl or crotonoyl.

When X or Y is an aralkyl group optionally substituted in its aryl moiety, it may suitably be an aralkyl group having 7 or 8 carbon atoms, the aryl moiety of which is optionally substituted with up to 3 substituents, said substituents being the same or different from each other and being one or more of chlorine, $C_{1-4}$ alkyl or $C_{1-8}$ alkoxy, e.g., benzyl, phenethyl, o-, m- or p-chlorobenzyl, o-, m- or p-methylbenzyl, p-isopropylbenzyl, p-t-butylbenzyl, p-methoxybenzyl, p-butoxybenzyl or p-octoxybenzyl; and it is preferably benzyl.

When X or Y is a group of the formula -$CH_2CH(R^1)OR^2$ and $R^2$ is an aliphatic, aromatic, araliphatic or alicyclic acyl group, said acyl group can be represented by the formula -$COR^5$ wherein $R^5$ is suitably an alkyl group having from 1 to 17 carbon atoms, e.g., methyl, ethyl, propyl, isopropyl, butyl, heptyl, 1-ethylpentyl, nonyl, undecyl or heptadecyl, an alkenyl group having from 2 to 4 carbon atoms, e.g., vinyl, 1-propenyl, isopropenyl, 2-methyl1-propenyl or 1-butenyl, a phenyl group which may optionally be substituted with up to three substituents, said substituents being the same or different from each other and being one or more of chlorine, $C_{1-4}$ alkyl, $C_{1-8}$ alkoxy or hydroxy, e.g, phenyl, o-, m- or p-chlorophenyl, 2,4-dichlorophenyl, o-, m- or p-methylphenyl, p-isopropyl phenyl, p-t-butylphenyl, p-methoxyphenyl, p-ethoxyphenyl, p-butoxyphenyl, p-octoxyphenyl, 3,4,5-trimethoxyphenyl, o-hydroxyphenyl or 4-hydroxy-3,5-di-t-butylphenyl, an aralkyl group having 7 or 8 carbon atoms which may optionally be substituted with up to three substituents in its aryl moiety, said substituents being the same or different from each other and being one or more of chlorine, $C_{1-4}$ alkyl, $C_{1-8}$ alkoxy or hydroxy, e.g., benzyl, phenethyl, p-methylbenzyl or 4-hydroxy-3,5-di-t-butylphenethyl, a styryl group, or a cyclohexyl group. The group -$CH_2CH(R^1)OR^2$ is preferably one of the formula -$CH_2CH_2OR^6$ wherein $R^6$ represents a hydrogen atom or an acyl group having the formula -COR⁷, in which R⁷ is an alkyl group having from 1 to 17 carbon atoms, an alkenyl group having from 2 to 4 carbon atoms, a phenyl group, a p-t-butylphenyl group, a 4-hydroxy-3,5-di-t-butylphenyl group or a 4-hydroxy-3,5-di-t-butylphenethyl group, most preferably a group of the formula -CH$_2$CH$_2$-OR⁸, wherein R⁸ represents a hydrogen atom or an acyl group of the formula -COR⁹, and R⁹ represents an alkyl group having from 1 to 17 carbon atoms or a phenyl group.

When X or Y is a group of the formula -CH$_2$COOR³, R³ may suitably be an alkyl group having from 1 to 18 carbon atoms, e.g., methyl, ethyl, isopropyl, butyl, isobutyl, t-butyl, isopentyl, octyl, dodecyl or octadecyl, an alkenyl group having from 3 to 6 carbon atoms, e.g., allyl, 2-butenyl or 2-hexenyl, a phenyl group, an aralkyl group having 7 or 8 carbon atoms, e.g., benzyl or phenethyl, or a cyclohexyl group; and it is preferably an alkyl group having from 1 to 18 carbon atoms, most preferably from 1 to 4 carbon atoms.

When X or Y is a group of the formula —COOR⁴, R⁴ may suitably be an alkyl group having from 1 to 8 carbon atoms, e.g., methyl, ethyl, isobutyl or octyl, a benzyl group, a phenyl group, or a cyclohexyl group; and it is preferably an alkyl group having from 1 to 4 carbon atoms.

The compounds of the invention can exist in the form of different stereoisomers, and the individual stereoisomers as well as their mixtures are included within the scope of the invention.

The acid addition salts of the compounds of formula (I) are also included within the scope of the invention. There is no particular limitation on the acid forming these salts, provided that the choice of acid does not adversely affect the stabilizing properties of the salts when they are used to stabilize organic substrates. Acids which can be used include inorganic acids, such as, sulphuric, hydrochloric or phosphoric acid; organic carboxylic acids, such as, formic, acetic, valeric, stearic, oxalic, adipic, sebacic, maleic, benzoic, p-t-butylbenzoic, 4-hydroxy-3,5-di-t-butylbenzoic, salicyclic or terephthalic acid; sulphonic acids, such as, methanesulphonic or p-toluenesulphonic acid; and organic phosphonic acids, such as, phenylphosphonic acid.

A preferred class of the compounds of the invention are those of formula (I) wherein:

Z represents a hydrogen atom or a methyl group, especially a hydrogen atom; and

X and Y are identical and each represents a hydrogen atom, an alkyl group having from 1 to 4 carbon atoms, an alkenyl group having 3 or 4 carbon atoms, a 2-alkoxyethyl group having from 1 to 18 carbon atoms in its alkoxy moiety, an alkanoyl group having from 2 to 4 carbon atoms, an alkenoyl group having 3 or 4 carbon atoms, a 2,3-epoxypropyl group, a benzyl group, or a group of the formula —CH$_2$CH$_2$-OR⁸, wherein R⁸ has the meaning previously given, especially a hydrogen atom, a methyl group, a 2-hydroxyethyl group, an acetyl group, an acryloyl group or a crotonoyl group;

and acid addition salts thereof.

The most highly preferred acid addition salts are those formed with carboxylic acids.

The following is a non-limiting list of individual 4,4'-bipiperidylidene derivatives of formula (I). The numbers appended to the compounds in this list will be used to identify them hereinafter in the Examples.

1. 2,2,2',2',6,6,6',6'-octamethyl-4,4'-bipiperidylidene
2. 1,1', 2,2,2',2', 6,6,6',6'-decamethyl-4,4'-bipiperidylidene
3. 1,1'-diethyl-2,2,2',2', 6,6,6',6'-octamethyl-4,4'-bipiperidylidene
4. 1,1'-dibutyl-2,2,2', 2',2',6,6,6', 6'-octamethyl-4,4'-bipiperidylidene
5. 2,2,2', 2',6,6,6',6'-octamethyl-1,1'-dioctyl-4,4'-bipiperidylidene
6. 2,2,2',2',6,6,6',6'-octamethyl-1,1'-dioctadecyl-4,4'-bipiperidylidene
7. 1,1'-bis(2-hydroxyethyl)-2,2,2',2',6,6,6',6'-octamethyl-4,4'-bipiperidylidene
8. 1,1'bis(2-hydroxypropyl)-2,2,2',2',6,6,6',6'-octamethyl-4,4'-bipiperidylidene
9. 1,1'-bis(2-hydroxy-2-phenylethyl)-2,2,2',2',6,6,6',6'-octamethyl-4,4'-bipiperidylidene
10. 1,1'-bis(2-acetoxyethyl)-2,2,2',2', 6,6,6',6'-octamethyl-4,4'-bipiperidylidene
11. 1,1'-bis[2-(2-ethylhexanoyloxy)ethyl]-2,2,2', 2',6,6,6',', 6'-octamethyl-4,4'-bipiperidylidene
12. 2,2,2',2',6,6,6',6'-octamethyl-1,1'-bis(2-stearoyloxyethyl)-4,4'-bipiperidylidene
13. 1,1'-bis(2-acryloxyloxyethyl)-2,2,2',2',6,6,6',6'-octamethyl-4,4'-bipiperidylidene
14. 1,1'-bis(2-methacryloyloxyethyl)-2,2,2',2',6,6,6],6'-octamethyl-4,4-bipiperidylidene
15. 1,1'-bis(2-benzoyloxyethyl)-2,2,2',",,6,6,6',6'-octamethyl-4,4'-bipiperidylidene
16. 1,1'-bis{2[β-(4-hydroxy-3,5-di-t-butylphenyl)-propionyloxy]ethyl}-2,2,2', 2',6,6,6',6'-octamethyl-4,4'-bipiperidylidene
17. 1,1'-bis[2-(4-hydroxy-3,5-di-t-butylbenzoyloxy)ethyl]-2,2,2',2'-6,6,6',6'-octamethyl-4,4'-bipiperidylidene
18. 1,1'-bis(2-acetoxypropyl)-2,2,2',2',6,6,6',6'-octamethyl-4,4'-bipiperidylidene
19. 2,2,2',2',6,6,6',6'-octamethyl-1,1'-bis(2-stearoyloxypropyl)-4,4'-bipiperidylidene
20. 1,1'-bis(2,3-epoxypropyl)-2,2,2',2',6,6,6',6'-octamethyl-4,4'-bipiperidylidene
21. 1,1'-bis(2-ethoxyethyl)-2,2,2',2',6,6,6',6'-octamethyl-4,4'-bipiperidylidene
22. 1,1'-bis(ethoxycarbonylmethyl)-2,2,2',2',6,6,6',6'-octamethyl-4,4'-bipiperidylidene
23. 1,1'-diallyl-2,2,2',2',6,6,6',6'-octamethyl-4,4'-bipiperidylidene
24. 1,1'-di(2-butenyl)-2,2,2',2',6,6,6',6'-octamethyl-4,4'-bipiperidylidene
25. 1,1'-diacetyl-2,2,2',2',6,6,6',6'-octamethyl-4,4'-bipiperidylidene
26. 1,1'-diacryloyl-2,2,2',2',6,6,6',6'-octamethyl-4,4'-bipiperidylidene
27. 1,1'-dicrotonoyl-2,2,2',2',6,6,6',6'-octamethyl-4,4'-bipiperidylidene
28. 1,1'-dibenzyl-2,2,2',2',6,6,6',6'-octamethyl-4,4'-bipiperidylidene
29. 1,1'-bis(p-chlorobenzyl)-2,2,2',2',6,6,6',6'-octamethyl-4,4'-bipiperidylidene
30. 1,1'-diethoxycarbonyl-2,2,2',2',6,6,6',6'-octamethyl-4,4'-bipiperidylidene
31. 2,2,2',2',6,6,6',6'-octamethyl-4,4'-bipiperidylidene 1,1'-dioxyl
32. 1-butyl-2,2,2',2', 6,6,6',6'-octamethyl-4,4'-bipiperidylidene
33. 1'-butyl-1,2,2,2',2',6,6,6',6'-nonamethyl-4,4'-bipiperidylidene 34. 1-benzyl-1'-butyl-2,2,2',2',6,6,6',6'-octamethyl-4,4'-bipiperidylidene
35. 1-hydroxy-2,2,2',2',6,6,6',6'-octamethyl-4,4'-bipiperidylidene-1'-oxyl
36. 2,2',6,6'-tetraethyl-2,2',3,3',6,6'-hexamethyl-4,4'-bipiperidylidene
37. 2,2',6,6'-tetraethyl-1,1',2,2',3,3',6,6'-octamethyl-4,4'-bipiperidylidene
38. 2,2'-6,6'-tetraethyl-1,1'-bis(2-hydroxyethyl)-2,2',3,3',6,6'-hexamethyl-4,4'-bipiperidylidene
39. 1,1'-bis(2-acetoxyethyl)-2,2',6,6'-tetraethyl-2,2',3,3',6,6'-hexamethyl-4,4'-bipiperidylidene
40. 1,1'-dicyanomethyl-2,2,2',2',6,6,6',6'-octamethyl-4,4'-bipiperidylidene
41. 2,2,2',2',6,6,6',6'-octamethyl-1,1'-bis(2-octadecyloxyethyl)-4,4'-bipiperidylidene
42. 1,1'-dilauroyl-2,2,2',2',6,6,6',6'octamethyl-4,4'-bipiperidylidene
43. 1,1'-bis(2-cyclohexanoyloxyethyl)-2,2,2',2',6,6,6',6'-octamethyl-4,4'-bipiperidylidene
44. 1,1'-bis(2-cinnamoyloxyethyl)-2,2,2',2',6,6,6',6'-octamethyl-4,4'-bipiperidylidene
45. 1,1'-bis(2-butenyloxycarbonylmethyl)-2,2,2',2',6,6,6',6'-octamethyl-4,4'-bipiperidylidene
46. 2,2,2',2',6,6,6',6'-octamethyl-1,1'-bis(phenoxycarbonylmethyl)-4,4'-bipiperidylidene
47. 1,1'-bis(benzyloxycarbonylmethyl)-2,2,2',2',6,6,6',6'-octamethyl-4,4'-bipiperidylidene
48. 1,1'-bis(cyclohexyloxycarbonylmethyl)-2,2,2',2',6,6,6',6'-octamethyl-4,4'-bipiperidylidene
49. 1,1'-dibenzyloxycarbonyl-2,2,2',2',6,6,6',6'-octamethyl-4,4'-bipiperidylidene
50. 2,2,2',2',6,6,6',6'-octamethyl-1,1'-diphenoxycarbonyl-4,4'-bipiperidylidene
51. 1,1'-dicyclohexyloxycarbonyl-2,2,2',2',6,6,6',6'-octamethyl-4,4'-bipiperidylidene The compounds of the invention can be prepared by the following methods:

Method 1

Compounds of formula (I) wherein X and Y are identical and each represents a hydrogen atom, i.e., compounds having the formula

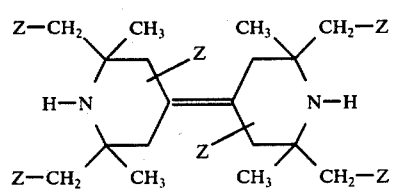

(II)

wherein Z has the meaning previously given, can be prepared by heating a compound of formula

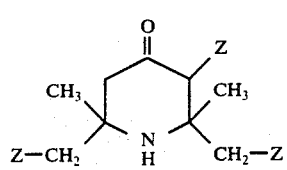

(III)

wherein Z has the meaning previously given in an inert solvent e.g., an ether, such as, tetrahydrofuran or dioxane, in the presence of a reductive condensing agent, such as, titanium tetrachloride/zinc, as disclosed in Chemistry Letters, Page 1041 (1973), or titanium trichloride/lithium aluminium hydride [J.A.C.S., 96, 4708 (1974)]. The reaction is advantageously carried out in the presence of an acid, such as, acetic or propionic acid, and is preferably carried out at ambient temperature or at the reflux temperature of the solvent used.

Method 2

Compounds of formula (I) wherein X and Y are identical and are other than hydrogen atoms can be prepared by introducing a substituent on the nitrogen atom of the piperidine nucleus in the compounds of formula (II). This substituent can be introduced by the following methods:

a. Compounds wherein the substituents are alkyl, alkenyl, alkoxyalkyl, cyanoalkyl, aliphatic acyl, 2,3-epoxypropyl, aralkyl optionally substituted in its aryl moiety, $-CH_2CH(R^1)OR^2$, wherein $R^1$ and $R^2$ have the meanings previously given, $-CH_2COOR^3$, wherein $R^3$ has the meaning previously given, or $-COOR^2$ wherein $R^4$ has the meaning previously given can be prepared by reacting the compound of formula (II) with a halide of the desired substituents.

The reaction will proceed in the presence or absence of an acid-binding agent, but is preferably carried out in the presence of an acid-binding agent, e.g., a base, preferably an inorganic base, such as, potassium carbonate or sodium carbonate or an organic tertiary amine, such as, triethylamine.

b. Compounds wherein the substituents are oxyl or hydroxy groups can be prepared by reacting the compound of formula (II) with a peroxide, such as, hydrogen peroxide or m-chloroperbenzoic acid. The use of a large quantity of peroxide gives a compound in which the substituent is an oxyl group.

c. Compounds wherein the substituents are $-CH_2CH(R^1)OH$, wherein $R^1$ has the meaning previously given, can also be prepared by reacting the compound of formula (II) with ethylene oxide, propylene oxide or styrene oxide, and by optionally further acylating the reaction product to obtain the corresponding acylated compounds.

d. Compounds wherein the substituents are methyl groups are preferably prepared by reacting the compound of formula (II) with formic acid and formaldehyde, by the Leuckart-Wallach reaction.

Method 3

Compounds wherein substituents X and Y are different from each other can be prepared by introducing a substituent on the nitrogen atom of one piperidine nucleus and then introducing a different substituent on the nitrogen atom of the other piperidine nucleus, using whichever of the methods (a), (b), (c) or (d) is appropriate for the substituent being introduced in each case.

Whichever of the Methods 1-3 is used for the preparation of the compounds of formula (I), if desired, the products can then be salified by conventional techniques, to obtain the acid addition salts thereof.

The compounds of formula (III), used as starting materials in the processes just described, can be prepared, for example, by the following reactions, which can be performed under per se known conditions wherein the symbols Z having the meaning previously given:

(IV)

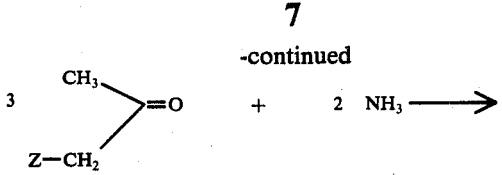

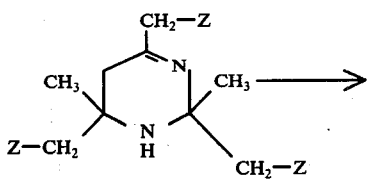

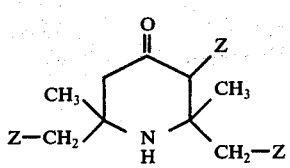

This preparation can be performed in two different ways, viz.:

A. The ketone of formula (IV) is treated with ammonia in an alcohol, over a prolonged period of time, by the method described in Berichte 41, 777 (1908); or B. The ketone of formula (IV) is reacted with ammonia in the presence of an acid catalyst, to give 1,2,5,6-tetrahydropyrimidine derivative of formula (V), by the method described in United States Patent Specification No. 2,516,626, and the compound of formula (V) is then treated with calcium chloride, an organic sulphonic acid, e.g., p-toluenesulphonic or benzenesulphonic acid, a mineral acid, e.g., hydrochloric or sulphuric acid, or an ammonium salt of a mineral acid, e.g. ammonium chloride or ammonium bromide, or a mixture thereof, in the presence of a small amount of water.

The following are examples of the 4-piperidone derivatives of formula (III) which can be obtained in this way.

2,2,6,6-tetramethyl-4-piperidone: Δ bp 95°–99° C/10 mmHg 2,6-diethyl-2,3,6-trimethyl-4-piperidone: bp 91°–93° C/2.0 mmHg 3-ethyl-2,6-dimethyl-2,6-dipropyl-4-piperidone: bp 115°–118° C/1.5 mmHg 2,6-diisobutyl-2,6-dimethyl-3-isopropyl-4-piperidone: bp 129°–131° C/2.0 mmHg.

The 4,4′-bipiperidylidene derivatives of the invention are useful for stabilizing organic substrates, especially synthetic and natural polymers, against photo- and/or thermal-deterioration. Organic substrates which can be stabilized in this way include:

olefin and diene polymers
inclucing homopolymers of olefins and dienes, e.g., low-density, high-density and cross-linked polyethylenes, polypropylene, polyisobutylene, polymethylbutene-1, polymethylpentene-1, polyisoprene and polybutadiene, mixtures of such homopolymers, e.g., mixtures of polypropylene and polyethylene, polypropylene and polybutene-1, or polypropylene and polyisobutylene, and copolymers of olefins and dienes, e.g., ethylene/propylene copolymers, propylene/butene-1 copolymers, propylene/isobutylene copolymers, ethylene/butene-1 copolymers, and terpolymers of ethylene and propylene with dienes, such as, hexadiene, dicyclopentadiene or ethylidene norbornene;

styrene polymers
including polystyrene, copolymers of styrene and of α-methylstyrene, e.g., styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength, and graft copolymers of styrene, e.g., polymers in which styrene is grafted onto polybutadiene, and polymers in which styrene and acrylonitrile are grafted onto polybutadiene as well as mixtures thereof with the aforementioned styrene copolymers commonly known as acrylonitrile/butadiene/styrene or ABS plastics;

halogenated vinyl and vinylidene polymers
including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids
and derivatives thereof, including polyacrylates and polymethacrylates, polyacrylic amides and polyacrylonitrile;

polymers derived from unsaturated alcohols and amines
and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers, e.g., ethylene/vinyl acetate copolymers;

epoxy polymers
including homopolymers and copolymers derived from epoxides, e.g., polyethylene oxide, and polymers derived from bis-glycidyl ethers;

polyacetals, polyalkylene oxides and polyphenylene oxides
including polyoxymethylene, oxymethylene/ethylene oxide copolymers, polyoxyethylene, polypropylene oxide, polyisobutylene oxide and polyphenylene oxides;

polyurethanes and polyureas;

polycarbonates;

polysulphones;

polyamides and copolyamides
derived from diamines and dicarboxylic acids and/or from aminocarboxylic acids or the corresponding lactams, including nylon-6, nylon-6,6, nylon-6,10, nylon-11 and nylon-12;

polyesters
derived from dicarboxylic acids and dialcohols and/or from hydroxycarboxylic acids and the corresponding lactones, e.g., polyethylene glycol terephthalate and poly-1,4-dimethylol-cyclohexane terephthalate;

cross-linked polymers derived from aldehydes together with phenols, ureas or melamines, e.g., phenol/formaldehyde, urea/formaldehyde and melamine/formaldehyde resins;

alkyl resins e.g., glycerol/phthalic acid resins and mixtures thereof with melamine/formaldehyde resins;

unsaturated polyester resins derived from copolyesters of saturated and unsaturated dicarboxylic acids with polyhydric alcohols as well as from vinyl compounds as cross-linking agents, and also halogenated flame-resistant modifications thereof; and natural polymers including cellulose, rubber and proteins, as well as chemically modified homologous thereof, e.g., cellulose acetates, cellulose propionates, cellulose butyrates and cellulose ethers such as methyl cellulose.

The amount of the stabilizers of the invention needed for effective stabilization of organic substrates will depend on a variety of factors, such as, the type and properties of the substrate concerned, its intended use, and the presence of other stabilizers. It is generally satisfactory to use from 0.01% to 5% by weight of the stabilizers of the invention, based on the weight of the substrate, but the most effective range will vary with the type of substrate: viz. 0.01 to 2.0%, preferably 0.02% to 1.0%, by weight of olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into the organic substrates by conventional techniques, at any convenient stage prior to the manufacture of shaped articles therefrom. For example, the stabilizer may be mixed with the substrate in dry powder form, or a suspension or emulsion of the stabilizer may be mixed with a solution, suspension or emulsion of the substrate.

Accordingly, the invention also provides a composition comprising an organic substrate, preferably a natural or synthetic polymer, and at least one of said compounds of formula (I) or acid addition salt thereof.

The stabilized compositions of the invention may optionally also contain various conventional additives, such as, the following Antioxidants Simple, 2,6-dialkylphenols, such as, for example, 2,6-di-t-butyl-4-methylphenol, 2-t-butyl-4,6-dimethylphenol, 2,6-di-t-butyl-4-methoxymethylphenol and 2,6-dioctadecyl-4-methylphenol.

Derivatives of alkylated hydroquinones, such as, for example, 2,5-di-t-butylhydroquinone, 2,5-di-t-amylhydroquinone, 2,6-di-t-butylhydroquinone, 2,5-di-t-butyl-4-hydroxyanisole, 3,5-di-t-butyl-4-hydroxyanisole, tris(3,5-di-t-butyl-4-hydroxyphenyl)phosphite, 3,5-di-y-butyl-4-hydroxyphenylstearate and di-(3,5-di-t-butyl-4-hydroxyphenyl)adipate.

Hydroxylated thiodiphenyl ethers, such as, for example, 2,2'-thiobis-(6-t-butyl-4-methylphenol), 2,2'-thiobis(4-octylphenol), 4,4'-thiobis-(6-t-butyl-3-methylphenol), 4,4'-thiobis (3,6-di-s-amylphenol), 4,4'-thiobis(6-t-butyl-2-methylphenol) and 4,4'-bis(2,6-dimethyl-4-hydroxyphenyl)disulphide.

Alkylidene-bisphenols, such as, for example, 2,2'-methylene-bis-(6-t-butyl-4-methylphenol), 2,2'-methylene-bis(6-t-butyl-4-ethylphenol), 4,4'-methylene-bis(6-t-butyl-2-methylphenol), 4,4'-methylene-bis-(2,5-di-t-butylphenol), 2,6-di-(3t-butyl-5-methyl-2-hydroxybenzyl)-4-methylphenol, 2,2'-methylene-bis[4-methyl-6-(α-methylcyclohexyl)-phenol], 1,1-bis(3,5-dimethyl-2-hydroxyphenyl)butane, 1,1-bis(5-t-butyl-4-hydroxy-2-methylphenyl)butane, 2,2-bis(5-t-butyl-4-hydroxy-2-methylphenyl)butane, 2,2-bis(3,5-di-t-butyl-4-hydroxyphenyl)propane, 1,1,3-tris(5-t-butyl-4-hydroxy-2-methylphenyl)butane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane and ethylene glycol bis [3,3-bis(3'-t-butyl-4'-hydroxyphenyl)butyrate].

O-, N- and S-benzyl compounds, such as, for example, 3,5,3', 5'-tetra-t-butyl-4,4'-dihydroxydibenzyl ether, 4-hydroxy-3,5-dimethylbenzyl-mercaptoacetic acid octadecyl ester, tri(3,5-di-t-butyl-4-hydroxybenzyl)amine, and bis(4t-butyl-3-hydroxy-2,6-dimethylbenzyl)-dithiolterephthalate.

Hydroxybenzylated malonic esters, such as, for example, 2,2-bis(3,5-di-t-butyl-2-hydroxybenzyl)malonic acid dioctadecyl ester 2-(3-t-butyl-4-hydroxy-5-methylbenzyl)malonic acid dioctadecyl ester, 2,2-bis(3,5-di-t-butyl-4-hydroxybenzyl)malonic acid didodecylmercaptoethyl ester, and 2,2-bis(3,5-di-t-butyl-4-hydroxybenzyl)-malonic acid di(4t-octylphenyl)ester.

Hydroxybenzyl aromatics, such as, for example, 1,3,5-tri(3,5-di-t-butyl-4-hydroxybenzyl)-2,4,6-trimethylbenzene, 1,4-di(3,5-di-t-butyl-4-hydroxybenzyl)-2,3,5,6-tetramethylbenzene, and 2,4,6-tri-(3,5-di-t-butyl-4-hydroxybenzyl)phenol.

-s-Triazine compounds such as, for example, 2,4-bis-octylmercapto 6-(3,5-di-t-butyl-4-hydroxyanilino)-s-triazine, 2-octylmercapto-4,6-bis(3,5di-t-butyl-4-hydroxyanilino)-s-triazine, 2-octylmercapto-4,6-bis(3,5-di-t-butyl-4-hydroxyphenoxy)-s-triazine, 2,4,6-tris(3,5di-t-butyl-4-hydroxyphenoxy)-s-triazine, 2,4,6-tris(3,5di-t-butyl-4-hydroxyphenylethyl)-s-triazine, and 1,3,5-tris(3,5-di-t-butyl-4-hydroxybenzyl)isocyanurate.

Amides of 3,5-di-t-butyl-4-hydroxyphenylpropionic acid, such as, for example, 1,3,5-tris(3,5-di-t-butyl-4-hydroxyphenyl-propionyl)-hexahydro-s-triazine, and N,N'-bis(3,5-di-t-butyl-4-hydroxyphenylpropionyl)-hexamethylenediamine.

Esters of 3,5-di-t-butyl-4-hydroxyphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane trimethylolpropane, trishydroxyethyl isocyanurate, and 4-hydroxymethyl-1-phospha-2,6,7-trioxabicyclo[2,2,2]octane.

Esters of 5-t-butyl-4-hydroxy-3-methylphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia- pentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane Esters of 3,5-di-t-butyl-4-hydroxyphenylacetic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethyloletane, trimethylolpropane, trishydroxyethyl isocyanurate, and 4-hydroxymethyl-1-phospha-2,6,7-trioxabicyclo-[2,2,2]octane.

Acylaminophenols, such as, for example, N-(3,5-di-t-butyl-4-hydroxyphenyl)stearic acid amide and N,N'-bis(3,5-di-t-butyl-4-hydroxyphenyl)thiobisacetamide.

Benzylphosphonates, such as, for example, 3,5-di-t-butyl-4-hydroxybenzylphosphonic acid dimethyl ester, 3,5-di-t-butyl-4-hydroxybenzylphosphonic acid diethyl ester, 3,5di-t-butyl-4-hydroxybenzylphosphonic acid dioctadecyl ester, and 5-t-butyl-4-hydroxy-3methylbenzylphosphonic acid dioctadecyl ester Aminoaryl derivatives, such as, for example, phenyl-1-naphthylamine, phenyl-2-naphthylamine, N,N'-diphenyl-p-phenylenediamine, N,N'-di-3-naphthyl-p-phenylenediamine, N,N'-di-s-butyl-p-phenylendiamine,-6-ethoxy-2,2,4-trimethyl-1,2-dihydroquinoline, 6-dodecyl-2,2,4-trimethyl-1,2-dihydroquinoline, mono- and di-octyliminodibenzyl, and polymerized 2,2,4-trimethyl-1,2-dihydroquinoline.

Metal deactivators, such as for example, oxanilide, isophthalic acid dihydrazide, sebacic acid bisphenylhydrazide, bisbenzylidene oxalic acid dihydrazide, N,N'-diacetyladipic acid dihydrazide, N,N'-bis-salicyloyloxalic acid dihydrazide, N,N'-bis-salicyloylhydrazine, and N,N'-bis-(3,5-di-t-butyl-4-hydroxyphenylpropionyl)hydrazine.

Peroxide deactivators, such as, for example, esters of β-thiodipropionic acid, e.g., the lauryl, stearyl, myristyl and tridecyl esters, salts of 2-mercaptobenzimidazole, e.g., the zinc salt, and diphenylthioruea.

Polyamide stabilizers, such as, for example, copper salts in combination with iodides and/or phosphorus compounds and salts of divalent manganese.

Basic co-stabilizers, such as, for example, polyvinylpyrrolidone, melamine, benzoguanamine, triallyl cyanurate, dicyandiamide, urea derivatives, hydrazine derivatives, amines, polyamides polyurethanes, and alkali metal salts and alkaline earth metal salts of higher saturated or unsaturated fatty acids, e.g., Ca stearate, Mg laurate, Na riconoleate, K palmitate and Zn stearate.

PVC stabilizers, such as, for example, organic tin compounds, organic lead compounds and Ba/Cd salts of fatty acids.

Nucleating agents, such as, for example, 4-t-butylbenzoic acid, adipic acid, and diphenylacetic acid.

The use of stabilizers of the invention with the above-listed antioxidants is particularly effective for the stabilization of olefin polymers.

The invention is illustrated by the following Preparations and Examples, in which all parts and percentages are by weight. Preparations A and B illustrate the preparation of the starting materials of formula (III); Examples 1 to 7 illustrate the preparation of compounds of the invention; and Example 8 illustrates the stabilization of synthetic polymers by means of compounds of the invention which are identified by the numbers appended to them in the list given hereinbefore.

Preparation A 2,6-diethyl-2,3,6-trimethyl-4-piperidone

First 14.7 g of powdered calcium chloride dihydrate and then 3 ml of water were added to an ice-cooled mixture of 39.2 g of 2,4,6-triethyl-2,6-dimethyl-1,2,5,6-tetrahydropyrimidine and 18.0g of methyl ethyl ketone. The resulting mixture was heated at 60° C with stirring for 15 hours made alkaline with 35% aqueous sodium hydroxide solution, and extracted with diethyl ether. The extract was dried over potassium carbonate and the ether was evaporated off. The residue was distilled under reduced pressure, to give 32.4 g of the desired product.

Preparation B 2,6-diethyl-2,3,6-trimethyl-4-piperidone 19.6 g of 2,4,6-triethyl-2,6-dimethyl-1,2,5,6-tetrahydropyrimidine and 0.4 g of ammonium bromide were added to 200 ml of methanol, and 10 g of 37% hydrochloric acid were added dropwise to the resulting mixture at 10° C, under stirring. After completion of the addition, the mixture was stirred at room temperature for 4 hours, and then 20 ml of 18% hydrochloric acid were added dropwise to it. The mixture was then heated at 30°– 40° C for 7 hours and allowed to stand overnight at room temperature. The mixture was made alkaline with 40% aqueous potassium carbonate solution; and, after the methanol had been evaporated off under reduced pressure, the mixture was extracted with diethyl ether. The extract was dried over potassium carbonate and the ether was removed. The residue was subjected to distillation under reduced pressure, to give 15.1 g of the desired compound as an oil boiling at 91°–93° C/2.0 mmHg.

EXAMPLE 1

2,2,2',2', 6,6,6', 6'-octamethyl-4,4'-bipiperidylidene 15.5 g of 2,2,6,6-tetramethyl-4-piperidone and 6 g of acetic acid were dissolved in 100 ml of dioxane. The solution was added at 5°– 10° C under stirring to a solution of 28.4 g of titanium tetrachloride in 150 ml of dioxane, and the mixture was stirred at the same temperature for 30 minutes. A suspension of 19.5 g of zinc powder in 50 ml of dioxane was added; and the mixture was stirred at 10°– 15° C for one hour, then at room temperature for 1 hour, and then refluxed for 8 hours. After cooling, the reaction mixture was neutralized with 10% aqueous potassium carbonate solution, then made strongly alkaline with 20% aqueous sodium hydroxide solution and extracted with benzene. The extract was dried over potassium carbonate and the solvent was removed. The resulting residue was recrystallized from petroleum ether, to give 12.5 g of the desired product as white crystals melting at 144°–145° C.

EXAMPLE 2

1,1',2,2,2', 2',6,6,6',6'-decamethyl4,4'-bipiperidylidene 15 g of formic acid were added dropwise to a mixture of 50 g of 30% aqueous formaldehye and 13.9 g of 2,2,2', 2'2',6,6,6'5,5,6', 6'-octamethyl-4,4'-bipiperidylidene, and the resulting mixture was heated at 80°- 90° C for 8 hours. After cooling, the reaction mixture was made alkaline with 30% aqueous potassium hydroxide solution, then extracted with benzene. The extract was dried over potassium carbonate and the solvent was removed under reduced pressure. The resulting residue was recrystallized from petroleum ether, to give 12.6 g of the desired product melting at 136°–137° C.

EXAMPLE 3

1,1'-diallyl-2,2,2',2',6,6,6',6'-octamethyl-4,4'-bipiperidylidene

A mixture of 5.6 g of 2,2,2',2',6,6,6',6'-octamethyl-4,4'-bipiperidylidene, 6.0 g of allyl bromide, 7.0 g of potassium carbonate and 50 ml of dimethylformamide was stirred at 105°–110° C for 10 hours. After completion of the reaction, the reaction mixture was concentrated under reduced pressure and the resulting residue was extracted with benzene. The extract was washed with 10% aqueous sodium carbonate solution, then dried over potassium carbonate. The solvent was removed from the extract and the resulting residue was purified by column chromatography on silica gel by elution with benzene, to give 3.5 g of the desired product as white crystals melting at 147°–148° C.

EXAMPLE 4

1,1'-diacryloyl-2,2,2',2',6,6,6',6'-octamethyl-4,4'-bipiperidylidene

A mixture of 5.6 g of 2,2,2',2',6,6,6',6'-octamethyl-4,4'-bipiperidylidene, 5.0 g of triethylamine and 50 ml of dimethylformamide was cooled to 5°–10° C, and 4.5 g of acrylyl chloride was added dropwise thereto. After completion of the addition, the mixture was stirred at room temperature for one hour and then at 105°–110° C for 3 hours. After completion of the reaction, the reaction mixture was concentrated under reduced pressure and the resulting residue was extracted with benzene. The extract was washed with 10% aqueous sodium carbonate solution and dried over potassium carbonate. The residue was purified by column chromatography on silica gel (eluted with a 10:1 mixture of benene and ethyl acetate), then by recrystallization from a 5:1 mixture of isopropyl ether and benzene, to give 1.2 g of the desired product melting at 196°–198° C.

EXAMPLE 5

1,1'-bis(2-hydroxyethyl)-2,2,2',2',6,6,6',6'-octamethyl-4,4'-bipiperidylidene

A mixture of 41.7 g of 2,2,2',2',6,6,6',6'-octamethyl-4,4'-bipiperidylidene, 100g of ethylene oxide, 700 ml of ethanol and 0.06 g of concentrated hydrochloric acid was stirred at 105°–110° C for 10 hours in an autoclave. After completion of the reaction, the reaction mixture was concentrated, and the resulting residue was recrystallized from benzene, to give 37.2 g of the desired product as white crystals melting at 226.5°–227.5° C.

EXAMPLE 6

2,2,2',2',6,6,6',6'-octamethyl-1,1'-bis(2-stearoyloxyethyl)-4,4'-bipiperidylidene A mixture of 3.7 g of 1,1'-bis(2-hydroxyethyl)-2,2,2',2'6,6,6',6'-octamethyl-4,4'-bipiperidylidene, 6.5 g of ethyl stearate, 0.03 g of lithium amide and 600 ml of xylene was heated under stirring for 10 hours, while 330 ml of the solvent was distilled off. After completion of the reaction, the reaction mixture was washed with water and dried over potassium carbonate. The reaction mixture was concentrated, and the resulting residue was recrystallized from hexane, to give 6.4 g of the desired product as white crystals melting at 76°–78° C.

EXAMPLE 7

1'-hydroxy-2,2,2',2',6,6,6',6'-octamethyl-4,4'-bipiperidylidene-1-oxyl 15.0 g of m-chlorobenzoyl hydroperoxide were added dropwise at 10°–15° C over a period of one hour to a solution of 5.0 g of 2,2,2',2',6,6,6',6'-octamethyl-4,4'-bipiperidylidene in 150 ml of methylene chloride. The mixture was stirred at room temperature for 5 hours, then allowed to stand overnight. After completion of the reaction the reaction mixture was washed successively with 10% aqueous potassium carbonate solution and water, and dried over potassium carbonate. The reaction mixture was concentrated and the resulting residue was recrystallized from benzene, to give 3.9 g of the desired product as light red crystals melting at 206°–208° C.

The following compounds were prepared, by substantially the same methods:

1,1'-diethyl-2,2,2',2',6,6,6',6'-octamethyl-4,4'-bipiperidylidene; mp 162°–163° C
1,1'-dibutyl-2,2,2',2',6,6,6',6'-octamethyl-4,4'-bipiperidylidene: mp 154°–155.5° C
1,1'-bis(2-acetoxyethyl)-2,2,2',2',6,6,6',6'-octamethyl-4,4'-bipiperidylidene: mp 133°–134° C
1,1'-bis(2-benzoyloxyethyl)-2,2,2',2',6,6,6',6'-octamethyl-4,4'-bipiperidylidene: mp 216.5°–218° C
1,1'-bis(2,3-epoxypropyl)-2,2,2',2',6,6,6',6'-octamethyl-4,4'-bipiperidylidene: mp 189°–190° C
1,1'-diacetyl-2,2,2',2',6,6,6',6'-octamethyl-4,4'-bipiperidylidene: mp 215°–216.5° C
1,1'-dibenzyl-2,2,2',2',6,6,6',6'-octamethyl-4,4'-bipiperidylidene: mp 264°–265° C
1-butyl-2,2,2',2',6,6,6',6'-octamethyl-4,4'-bipiperidylidene: mp 114.5°–116° C
2,2',6,6'-tetraethyl-2,2',3,3',6,6'-hexamethyl-4,4'-bipiperidylidene: bp 143°–145° C/0.006 mmHg
2,2',6,6'-tetraethyl-1,1',2,2',3,3',6,6'-octamethyl-4,4'-bipiperidylidene: bp 170°–172° C/3 mmHg

EXAMPLE 8

Stabilization of polypropylene

Mixtures were made from 100 parts of unstabilized polypropylene (MFI=18), 0.2 part of octadecyl $\beta$-(4-hydroxy-3,5-di-t-butylphenyl)propionate and 0.25 part of each in turn of the stabilizers of the invention indicated in the following table. The resulting mixtures were homogeneously blended and melted at 200°C, and moulded at 260° C under pressure into films 0.1 mm thick. Control sheets containing no stabilizer or containing the known UV-absorber 2-(2-hydroxy-3,5-di-t-butylphenyl)-5-chlorobenzo-1,2,3-triazole (trade name "Tinuvin 327") were also made in a similar manner.

The sheets thus formed were exposed to ultraviolet irradiation at 45° C in the "Standard Fade-Meter Type FA-1" manufactures and sold by Toyo Rika Instruments, Japan (a modification of the Atlas Fade-O-Meter Type FDA-R, which meets the requirement prescribed in paragraph 3.8 of Japanese Industrial Standard 1044-

L), and their brittleness time was measured. The results are given in the following table.

Table

| Stabilizer compound No. | Brittleness time (hours) |
|---|---|
| 1 | 1120 |
| 2 | 920 |
| 4 | 800 |
| 7 | 800 |
| 10 | 720 |
| 20 | 800 |
| 25 | 720 |
| 26 | 900 |
| 28 | 900 |
| 32 | 880 |
| 36 | 800 |
| 37 | 1100 |
| "Tinuvin 327" | 320 |
| none | 120 |

We claim:

1. A 4,4'-bipiperidylidene compound having the formula (I):

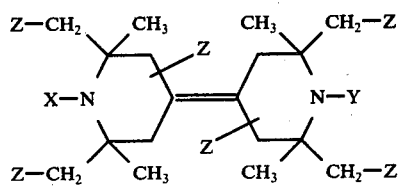

wherein
 each of the symbols Z represents
  a hydrogen atom, or
  an alkyl group having from 1 to 3 carbon atoms; and
 X and Y are the same or different and each represents
  a hydrogen atom,
  an oxyl group,
  a hydroxy group,
  an alkyl group having from 1 to 18 carbon atoms,
  an alkenyl group having from 3 to 6 carbon atoms,
  an alkoxyalkyl group having from 1 to 3 carbon atoms in its alkyl moiety and from 1 to 18 carbon atoms in its alkoxy moiety,
  a cyanoalkyl group having 2 or 3 carbon atoms,
  an alkanoyl group having from 1 to 12 carbon atoms,
  an alkenoyl group having 3 or 4 carbon atoms,
  an 2,3-epoxypropyl group,
  an unsubstituted aralkyl group having 7 or 8 carbon atoms,
  an aralkyl group having 7 or 8 carbon atoms and having in its aryl moiety up to 3 substituents selected from the group consisting of chlorine atoms, $C_{1-4}$ alkyl groups and $C_{1-8}$ alkoxy groups,
  a group of the formula —CH$_2$CH(R$^1$)OR$^2$
  wherein
   R$^1$ represents
    a hydrogen atom,
    a methyl group, or
    a phenyl group, and
   R$^2$ represents
    a hydrogen atom, or
    an acyl group having the formula —COR$^5$
   wherein
    R$^5$ represents
     an alkyl group having from 1 to 17 carbon atoms,
     an alkenyl group having from 2 to 4 carbon atoms,
     an unsubstituted phenyl group,
     a phenyl group having up to 3 substituents selected from the group consisting of
    chlorine atoms,
    $C_{1-4}$ alkyl groups,
    $C_{1-8}$ alkoxy groups and
    hydroxy groups,
     an unsubstituted aralkyl group having 7 or 8 carbon atoms,
     an aralkyl group having 7 or 8 carbon atoms and having in its aryl moiety up to 3 substituents selected from the group consisting of
    chlorine atoms,
    $C_{1-4}$ alkyl groups,
    $C_{1-8}$ alkoxy groups, and hydroxy groups,
     a styryl group, or
     a cyclohexyl group,
  a group of the formula —CH$_2$COOR$^3$
  wherein
   R$^3$ represents
    an alkyl group having from 1 to 18 carbon atoms,
    an alkenyl group having from 3 to 6 carbon atoms,
    a phenyl group,
    an aralkyl group having 7 or 8 carbon atoms, or
    a cyclohexyl group, or
  a group of the formula —COOR$^4$
  wherein
   R$^4$ represents
    an alkyl group having from 1 to 8 carbon atoms,
    a benzyl group,
    a phenyl group, or
    a cyclohexyl group
and an acid addition salt thereof.

2. A compound as claimed in claim 1 wherein:
 each of the symbols Z represents a hydrogen atom or a lower alkyl group having from 1 to 3 carbon atoms; and
 X and Y are the same or different and each represents a hydrogen atom; an oxyl group; a hydroxy group; an alkyl group having from 1 to 18 carbon atoms; an alkenyl group having from 3 to 6 carbon atoms; an alkoxyalkyl group having from 1 to 3 carbon atoms in its alkyl moiety and from 1 to 18 carbon atoms in its alkoxy moiety; a cyanoalkyl group having 2 or 3 carbon atoms; an alkanoyl group having from 2 to 4 carbon atoms; an alkenoyl group having 3 or 4 carbon atoms; an unsubstituted aralkyl group having 7 or 8 carbon atoms; an aralkyl group having 7 or 8 carbon atoms and up to 3 substituents selected from the group consisting of chlorine atoms, $C_{1-4}$ alkyl groups and $C_{1-8}$ alkoxy groups; a group of the formula —CH$_2$CH$_2$OR$^6$, wherein R$^6$ represents a hydrogen atom or an acyl group having the formula —COR$^7$ in which R$^7$ is an alkyl group having from 1 to 17 carbon atoms, an alkenyl group having from 2 to 4 carbon atoms, a phenyl group, a p-t-butylphenyl group, a 4-hydroxy-3,5-di-t-butylphenyl group or a 4-hydroxy-3,5-di-t-butylphenethyl group; a group of the formula —CH$_2$COOR$^3$, wherein R$^3$ represents an alkyl group having from 1 to 18 carbon atoms; or a group of the formula -COOR$^4$, wherein R$^4$ represents an alkyl group having from 1 to 4 carbon atoms.

3. A compound as claimed in claim 1, wherein:
each of the symbols Z represents a hydrogen atom or a methyl group; and
X and y are identical and each represents a hydrogen atom, an alkyl group having from 1 to 4 carbon atoms, an alkenyl group having 3 or 4 carbon atoms, a 2-alkoxyethyl group having from 1 to 18 carbon atoms in its alkoxy moiety, an alkanoyl group having from 2 to 4 carbon atoms, an alkenoyl group having 3 or 4 carbon atoms, a 2,3-epoxypropyl group, a benzyl group, or a group of the formula -CH$_2$CH$_2$-OR$^8$, wherein R$^8$ represents a hydrogen atom or an acyl group of the formula -COR$^9$ in which R$^9$ represents an alkyl group having from 1 to 17 carbon atoms or a phenyl group.

4. An acid addition salt of the compounds as claimed in claim 1 with carboxylic acids.

5. A compound as claimed in claim 1, wherein selected from the group consisting of:
2,2,2',2',6,6,6',6'-octamethyl-4,4'-bipiperidylidene;
1,1',2,2,2',2', 6,6, 6', 6'-decamethyl-4,4'-bipiperidylidene;
1,1'-dibutyl-2,2,2',2',6,6,6',6'-octamethyl-4,4'-bipiperidylidene;
1,1'-bis(2-hydroxyethyl)-2,2,2',2', 6,6,6',6'-octamethyl-4,4'-bipiperidylidene;
1,1'-bis(2-acetoxyethyl)-2,2,2',2',6,6,6',6'-octamethyl-4,4'-bipiperidylidene;
1,1'-bis(2,3-epoxypropyl)-2,2,2',2',6,6,6',6'-octamethyl-4,4'-bipiperidylidene;
1,1'-diacetyl-2,2,2',2',6,6,6',6'-octamethyl-4,4'-bipiperidylidene;
1,1'-diacryloyl-2,2,2',2',6,6,6',6'-octamethyl-4,4'-bipiperidylidene;
1,1'-dibenzyl-2,2,2',2',6,6,6',6'-octamethyl-4,4'-bipiperidylidene;
1-butyl-2,2,2',2', 6,6,6',6'-octamethyl-4,4'-bipiperidylidene;
2,2',6,6'-tetraethyl-2,2',3,3',6,6'-hexamethyl-4,4'-bipiperidylidene;
and
2,2,',6,6'-tetraethyl-1,1',2,2',3,3',6,6'-octamethyl-4,4'-bipiperidylidene.

6. A compound as claimed in claim 1 selected from the group consisting of:
1,1'-diethyl-2,2,2',2',6,6,6',6'-octamethyl-4,4'-bipiperidylidene;
1,1'-diallyl-2,2,2',2',6,6,6',6'-octamethyl-4,4'-bipiperidylidene;
2,2,2',2',6,6,6',6'-octamethyl-1,1'-bis(2-stearoyloxyethyl)-4,4'-bipiperidylidene;
1'-hydroxy-2,2,2',2',6,6,6',6'-octamethyl-4,4'-bipiperidylidene-1-oxyl; and
1,1'-bis(2-benzoyloxyethyl)-2,2,2',2',6,6,6',6'-octamethyl-4,4'-bipiperidylidene.

7. An organic polymer composition stabilized against photo- and thermal deterioration by the incorporation of a stabilizing amount of a 4,4'-bipiperidylidene derivative having the formula (I)

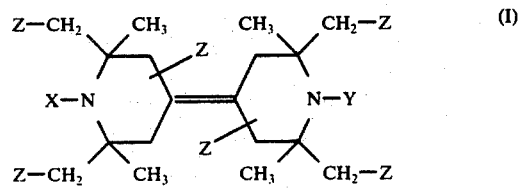

wherein
each of the symbols Z represents a hydrogen atom, or an alkyl group having from 1 to 3 carbon atoms, and
X and y are the same or different and each repesents
a hydrogen atom,
an oxyl group,
a hydroxy group,
an alkyl group having from 1 to 18 carbon atoms,
an alkenyl group having from 3 to 6 carbon atoms,
an alkoxyalkyl group having from 1 to 3 carbon atoms in its alkyl moiety and from 1 to 18 carbon atoms in its alkoxy moiety;
a cyanoalkyl group having 2 or 3 carbon atoms,
an alkanoyl group having from 1 to 23 carbon atoms,
an alkenoyl group having 3 or 4 carbon atoms,
an 2,3-epoxypropyl group,
an unsubstituted aralkyl group having 7 or 8 carbon atoms,
an aralkyl group having 7 or 8 carbon atoms and having in its aryl moiety up to 3 substituents selected from the group consisting of
chlorine atoms,
C$_{1-4}$ alkyl groups and
C$_{-8}$ alkoxy groups,
a group of the formula -CH$_2$CH(R$^1$)OR$^2$
wherein
R$^1$ represents
a hydrogen atom,
a methyl group, or
a phenyl group, and
R$^2$ represents
a hydrogen atom, or
an acyl group having the formula -COR$^5$
wherein
R$^5$ represents
an alkyl group having from 1 to 17 carbon atoms,
an alkenyl group having from 2 to 4 carbon atoms,
an unsubstituted phenyl group,
a phenyl group having up to 3 substituents selected from the group consisting of chlorine atoms,
C$_{1-4}$ alkyl groups,
C$_{1-8}$ alkoxy groups and
hydroxy groups,
an unsubstituted aralkyl group having 7 or 8 carbon atoms,
an aralkyl group having 7 or 8 carbon atoms and having in its aryl moiety up to 3 substituents selected from the group consisting of chlorine atoms,
C$_{1-4}$ alkyl groups,
C$_{1-8}$ alkoxy groups and hydroxy groups,
a styryl group, or
a cyclohexyl group,
a group of the formula -CH$_2$COOR$^3$
wherein
R$^3$ represents
an alkyl group having from 1 to 18 carbon atoms,
an alkenyl group having from 3 to 6 carbon atoms,
a phenyl group,
an aralkyl group having 7 or 8 carbon atoms, and
a cyclohexyl group, or
a group of the formula -COOR$^4$
wherein
R$^4$ represents an alkyl group having from 1 to 8 carbon atoms,
a benzyl group,
a phenyl group, or
a cyclohexyl group,
and an acid addition salt thereof.

8. A stabilized polymer composition as claimed in claim 7, wherein:
each of the symbols Z represents a hydrogen atom or a lower alkyl group having from 1 to 3 carbon atoms; and
X and y are the same or different and each represents a hydrogen atom; an oxyl group; a hydroxy group; an alkyl group having from 1 to 18 carbon atoms; an alkenyl group having from 3 to 6 carbon atoms; an alkoxyalkyl group having from 1 to 3 carbon atoms in its alkyl moiety and from 1 to 18 carbon atoms in its alkoxy moiety; a cyanoalkyl group having 2 or 3 carbon atoms; an alkanoyl group having from 2 to 4 carbon atoms; an alkenoyl group having 3 or 4 carbon atoms; an unsubstituted aralkyl group having 7 or 8 carbon atoms; an aralkyl group having 7 or 8 carbon atoms and up to 3 substituents selected from the group consisting of chlorine atoms, $C_{1-4}$ alkyl groups and $C_{1-8}$ alkoxy groups; a group of the formula $-CH_2CH_2OR^6$, wherein $R^6$ represents a hydrogen atom or an acyl group having the formula $-COR^7$ in which $R^7$ is an alkyl group having from 1 to 17 carbon atoms, an alkenyl group having from 2 to 4 carbon atoms, a phenyl group, a p-t-butylphenyl group, a 4-hydroxy-3,5-di-t-butylphenyl group or a 4-hydroxy-3,5-di-t-butylphenethyl group; a group of the formula $-CH_2COOR^3$ wherein $R^3$ represents an alkyl group having from 1 to 18 carbon atoms; or a group of the formula $-COOR^4$, wherein $R^4$ represents an alkyl group having from 1 to 4 carbon atoms.

9. A stabilized polymer composition as claimed in claim 7, wherein:
each of the symbols Z represents a hydrogen atom or a methyl group; and
X and Y are identical and each represents a hydrogen atom, an alkyl group haaving from 1 to 4 carbon atoms, an alkenyl group having 3 or 4 carbon atoms, a 2-alkoxyethyl group having from 1 to 18 carbon atoms in its alkoxy moiety, an alkanoyl group having from 2 to 4 carbon atoms, an alkenoyl group having 3 or 4 carbon atoms, a 2,3-epoxypropyl group, a benzyl group, or a group of the formula $-CH_2CH_2-OR^8$, wherein $R^8$ represents a hydrogen atom or an acyl group of the formula $-COR^9$ in which $R^9$ represents an alkyl group having from 1 to 17 carbon atoms or a phenyl group.

10. A stabilized polymer composition as claimed in claim 7, wherein said acid addition salts are salts with carboxylic acids.

11. A stabilized polymer composition as claimed in claim 7, wherein said polymer is an olefin polymer.

12. A stabilized polymer composition as claimed in claim 7, wherein said polymer is selected from the group consisting of styrene polymers, halogenated vinyl and vinylidene polymers, polyurethanes and polyamides.

13. A stabilized polymer composition as claimed in claim 7, comprising from 0.01% to 5% by weight of said 4,4'-bipiperidylidene derivative.

* * * * *